United States Patent [19]

Huber et al.

[11] Patent Number: 5,662,911

[45] Date of Patent: Sep. 2, 1997

[54] BENZODIAZEPINE PROTEIN CONJUGATES

[75] Inventors: Erasmus Huber, Finning; Christian Klein; Hans-Peter Josel, both of Weilheim; Bruno Zink, Uffing, all of Germany

[73] Assignee: Boehringer Mannheim GmbH, Mannheim, Germany

[21] Appl. No.: 590,830

[22] Filed: Jan. 24, 1996

[30] Foreign Application Priority Data

Feb. 2, 1995 [DE] Germany ............. 195 03 320.5

[51] Int. Cl.$^6$ ............. A61K 45/00; C07D 243/28
[52] U.S. Cl. ............. 424/278.1; 514/686; 530/402; 540/507; 540/512; 540/514
[58] Field of Search ............. 514/686; 530/402; 540/514, 512, 507; 424/278.1

[56] References Cited

U.S. PATENT DOCUMENTS

| 4,046,636 | 9/1977 | Ullmann et al. ............. 195/63 |
| 5,434,052 | 7/1995 | Khanna ............. 435/7.6 |

FOREIGN PATENT DOCUMENTS

| 1040547 | 3/1962 | United Kingdom . |
| 9323076 | 11/1993 | WIPO . |

OTHER PUBLICATIONS

Randall & Banziger, J. Med. Chem. 1965, 8 :815–812.
Current Protocols in Mol Bio, Ausubel et al., Eds (Green Pub. Ass. & Wiley–Interscience, 1992, p. 11.1.2).
Harlow & Lane, Antibodies, Cold Spring Harbor Lab, 1988, p. 72.

Primary Examiner—Lila Feisee
Assistant Examiner—Susan Ungar
Attorney, Agent, or Firm—Nikaido Marmelstein Murray & Oram LLP

[57] ABSTRACT

Benzodiazepine protein conjugates of the formula I

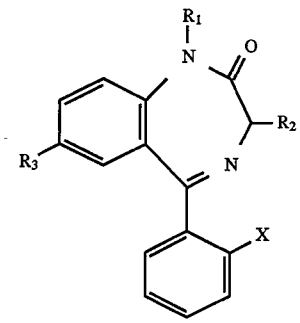

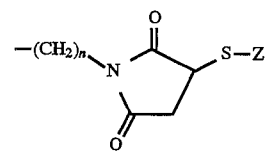

wherein R1 is hydrogen, a methyl group or R,
R2 is hydrogen, a hydroxyl or an OR group, with R1 or R2 containing an R group,
R3 is a halogen, NO2 or NH2,
X is hydrogen or a halogen,
wherein R is a group of the formula II, wherein Z is a macromolecular immunogen reactive carrier substance and n is 2 or 3.

The benzodiazepine protein conjugates are used as immunogens to obtain antibodies to benzodiazepines.

The invention also relates to an immunoassay for the detection of benzodiazepines where the so generated antibodies are used.

9 Claims, 1 Drawing Sheet

BENZODIAZEPINE PROTEIN CONJUGATES

The invention addresses benzoadiazepine protein conjugates, their preparation, their use as an immunogen, a method for the preparation of antibodies to benzodiazepines, and an immunoassay for the detection of benzodiazepines with the aid of these antibodies. Additional subject matters of the invention are new benzodiazepine linker connections, their preparation and use for the preparation of new conjugates.

The analytical detection of compounds of the benzodiazepine class has gained increasing importance over the last 1½ years. Benzodiazepines are important medicines, particularly tranquilizers, but can also be abused as drugs or substitute for hard drugs; they play an important role in case of intoxications, particularly mixed intoxications and suicides. Their detection is of great relevance in traffic-related medical questions.

There is, hence, a growing interest in immunological detection methods for the rapid, qualitative, and quantitative detection of benzodiazepines in body fluids. Immunoassays require benzodiazepine linker compounds capable of coupling ("hapten linker connections") for the synthesis of benzodiazepine protein conjugates ("hapten protein conjugates"). On the one hand, the benzodiazepine protein conjugates are used as immunogens for the generation of antibodies directed against benzodiazepines and, on the other hand, it is also possible to use benzodiazepine enzyme conjugates as enzyme-labeled antigens or polyhaptens in immunoassays.

Benzodiazepine linker compounds and benzodiazepine protein conjugates are known: EP-A-0 264 797, J. Pharm. Sci. 66, 235 (1977), Biochem. Pharm. Exp. Therapeutics 186, 167 (1973), J. Imm. 4, 135 (1983), U.S. Pat. No. 4,243,654, U.S. Pat. No. 4,046,636, U.S. Pat. No. 4,777,169, U.S. Pat. No. 4,043,989 and U.S. Pat. No. 4,083,948. The so generated antibodies are used in serum tests.

A particularity of immunoassays for the detection of benzodiazepine is that they require antibodies that are not only capable of recognizing certain benzodiazepine compounds, but also a large number of different relevant benzodiazepines (high cross reactivity). Another problem involved in the detection of benzodiazepines is to detect these substances in urine samples. Such samples contain metabolites of benzodiazepines (Clarke's Isolation and Identification of Drugs, 2nd ed., The Pharmaceutical Press, London 1986; R. C. Baselt, Disposition of Toxic Drugs and Chemicals in Man. 3rd ed., Year Book Medical Publishers Inc., 1989), especially amines, glucuronides, and benzophenon which are also to be detected by the antibodies used in the immunoassay. It was, hence, an object of the invention to provide immunogens in the form of benzodiazepine protein conjugates that generate as an immune response antibodies with a highest possible cross reactivity to relevant benzodiazepines, especially to benzodiazepine metabolites in the urine. Moreover, the invention is intended to provide immunogens in the form of benzodiazepine protein conjugates to generate antibodies whose binding capability is directed only to a small part to the linker structure of the conjugate.

The object is accomplished by the invention as covered in the claims.

Figure 1:
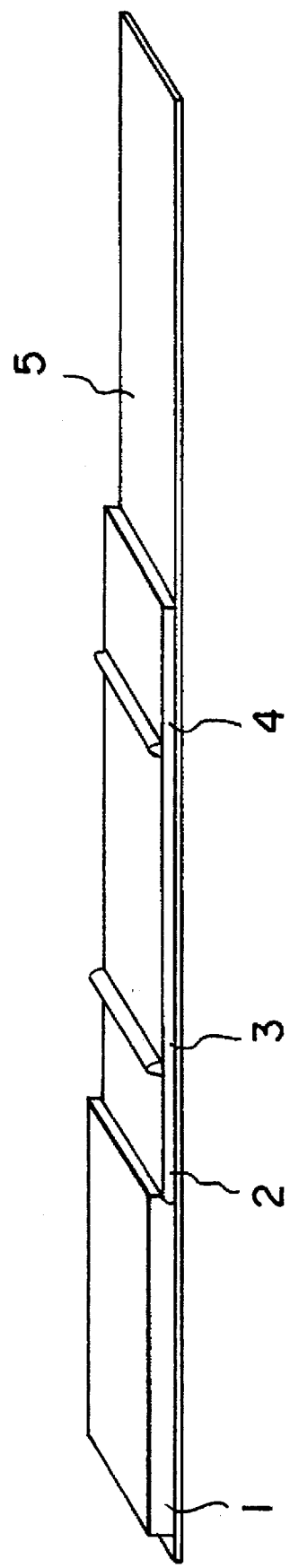
FIG. 1 shows a chromatography test strip in accordance with the present invention.

Subject matter of the invention are new benzodiazepine protein conjugates of the formula I wherein R1 is hydrogen, a methyl group or R; R2 is hydrogen, a hydroxyl or an OR group; R1 or R2 contain either an R group, R3 is halogen, NO2 or NH2, X is hydrogen or halogen, R being a group of the formula II wherein Z is a macromolecular immunogenically active carrier substance, and n=2 or 3.

In a preferred manner n=2.

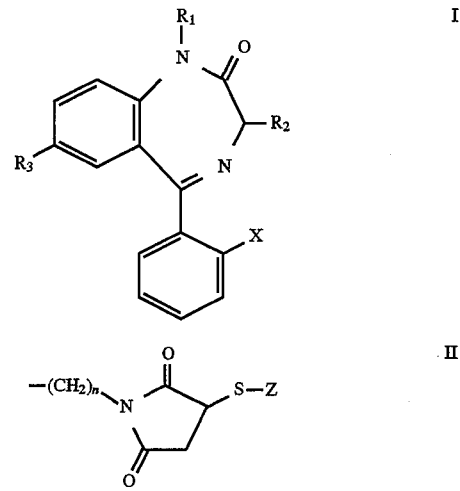

Macromolecular carrier substances are preferably polypeptides, such as KLH (key limpet haemocyanin), edestin, or bovine serum albumin. Enzymes such as β-galactosidase are also suitable.

Halogen is fluor, chloride, bromide, or iodine. A preferred residue for R3 and X is chloride.

A preferred residue for R3 is halogen, especially chloride.

Particularly preferred compounds of the formula are compounds of the formulas Ia and Ib.

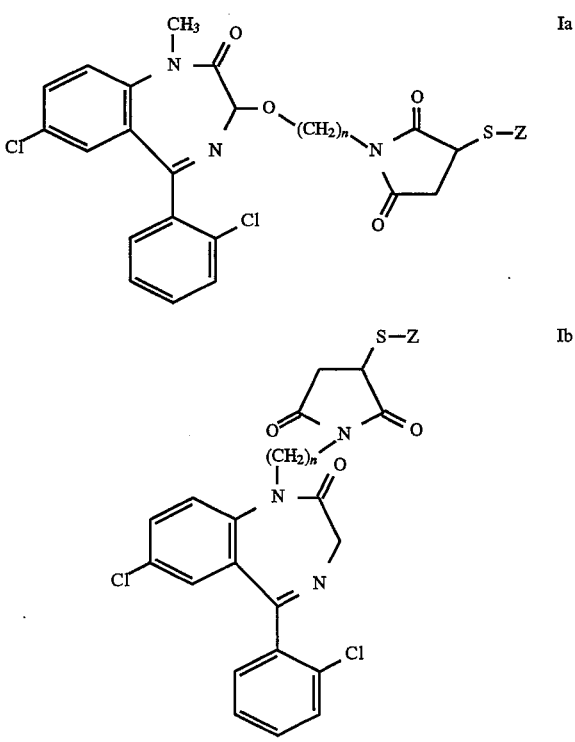

The conjugates in accordance with the invention are used as immunogens for the preparation of antibodies to benzodiazepines. Subject matter of the invention is a method for preparing antibodies to benzodiazepines by immunizing mammals and obtaining the so generated antibodies according to known methods, e.g. from the serum or the spleen, characterized in that a conjugate in accordance with the invention is used as an immunogen. The antiserum is prepared according to known methods, preferably in mice or sheep. Such an immunization procedure has been described by B. Dunkar, J. Agric. Food Chem. 38 (1990), 433–437 and N. H. Ogodrow, J. Agric. Food Chem. 38 (1990), 940–946.

Another subject matter of the invention are antibodies that can be obtained as the result of immunization using the benzodiazepine conjugates in accordance with the invention. These antibodies are monoclonal or preferably polyclonal antibodies.

The preparation of antibodies is accomplished by immunizing a laboratory animal with the immunogen. This step of the method of the invention can be accomplished in a conventional manner that is known to the expert. It is preferred to administer the immunogen to the laboratory animal in combination with an adjuvant. Freund's adjuvant or aluminum hydroxide together with Bordetella pertussis are particularly preferred. Immunization is carried out preferably over a period of several months in at least 4 immunizations in intervals of 4–6 weeks. The immunogen is preferably injected intraperitoneally.

B-lymphocytes that are fused with a permanent myeloma cell line are obtained from the so immunized animals. Fusion is carried out according to the method described by Köhler and Milstein (Nature 256. 1975, 495–497). The so formed primary cultures of hybrid cells are cloned in a conventional manner, e.g. using a commercially available cell sorter or by means of limited dilution. Those cultures are further processed which react positively to the benzodiazepine in a suitable testing method, e.g. an enzyme immunoassay (ELISA).

The antibodies show a high cross reactivity to temazepam, oxazepam, lorazepam, bromazepam, alprazolam, and to metabolites such as temazepam glucuronide or benzophenon, oxazepam glucuronide and amino flunitrazepam. They show, however, only little cross reactivity with respect to the linker bridge.

Another subject matter of the invention is the use of so obtained antibodies in immunoassays. The antibodies are in particular bound to a label (e.g. an enzyme, a radioactive label, or a particle such as latex or metal sol) or to another binding partner (e.g. streptavidin), or to a solid phase.

The method for the determination of the presence of benzodiazepine or benzodiazepine metabolites using the antibodies of the invention is carried out such that a sample, preferably urine, which is to be tested for the benzodiazepine, is brought into contact with at least one antibody of the invention which may be labeled or bound to a solid phase, or can be bound to a solid phase via another binding partner; the formation of the antibody benzodiazepine complex is determined in a suitable manner, for example, via a label.

The immunoassay is preferably carried out as a heterogeneous immunoassay, particularly preferred on a chromatography test strip as described in German laid-open application DE-OS 44 39 429 or DE-OS 40 24 919 (see FIG. 1).

Such a test strip preferably contains on one carrier foil (5) successively arranged absorbent zones: an analyte application zone (1), a conjugate zone (2), holding a labeled binding partner and, optionally, a binding partner with a specific binding site, e.g. biotin for the capture zone (3), then a capture zone (3) holding a capture reagent for the analyte or analyte antibody or a specific capture reagent for specific binding site of a binding partner, e.g. streptavidin, and a target zone (4) where the non-captured label is measured.

In case the immunoassay employed is one that is based on the sandwich principle, the application of the analyte onto the application zone in the conjugate zone produces a complex of analyte with a labeled antibody which can be bound via another antibody that is either bound to the solid phase or can be immobilized in the solid phase zone, where it is bound via a specific binding pair, e.g. biotin streptavidin.

When a competitive test is used, analyte and labeled analyte analog compete for an antibody that is bound to the solid phase in the capture zone or is bound to the solid phase via a specific binding site.

It is preferred to employ an immunoassay based on the IEMA analog test principle. In this test, the conjugate zone has a labeled antibody in excess to the analyte. Excess labeled antibodies are captured in a capture zone by the analyte analog while labeled analyte antibody complexes can be detected in the target zone.

Possible labels are conventional labels such as enzyme labels, fluorescence and dye labels, especially direct labels, particularly metal labels and particularly preferred gold labels.

The immunoassay provides rapid and exact results which also cover metabolites of benzodiazepines.

Another subject matter of the invention is a method for the preparation of the benzodiazepine protein conjugates in accordance with the invention. It is characterized in that benzodiazepine linker compounds of the formula III are reacted with a carrier substance compound, preferably with polypeptide compounds, which contain at least one thiol group to produce compounds of the formula I.

The polypeptide compounds per se can also contain SH groups. It is, however, also possible to synthetically incorporate SH groups in the polypeptide compounds according to methods that are known to the experts. The residues R3 and X and n in the formula III have the meaning given in formula I, R1' is hydrogen, methyl or R', R2' is hydrogen, a hydroxyl or an OR' group where R1' or R2' contain an R' group, and R' is a group of the formula IV.

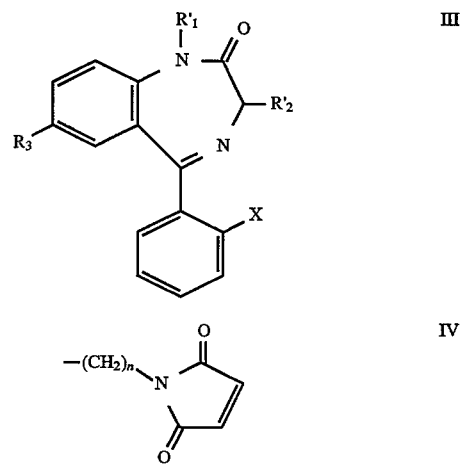

The benzodiazepine linker compounds of the formula III are novel. Another subject matter of the invention are, hence, these compounds and their use for the preparation of the benzodiazepine protein conjugates in accordance with the invention.

Another subject matter of the invention is a method for the preparation of the benzodiazepine linker compounds of the formula III.

If, in formula III, R2' is an OR'-group and R1' a hydrogen or CH3 group, the compounds are prepared according to the following reaction scheme:

with acetic acid anhydride (compounds of the formula VII). Compounds of this kind are described in U.S. Pat. No. 4,083,948. Subsequently, a reaction is carried out with the aid of an acid catalyst using N-protected ethanolamine or propanolamine (compounds of the formulas VIII and IX). Subsequently, ethoxycarbonylmaleimide, for example, is

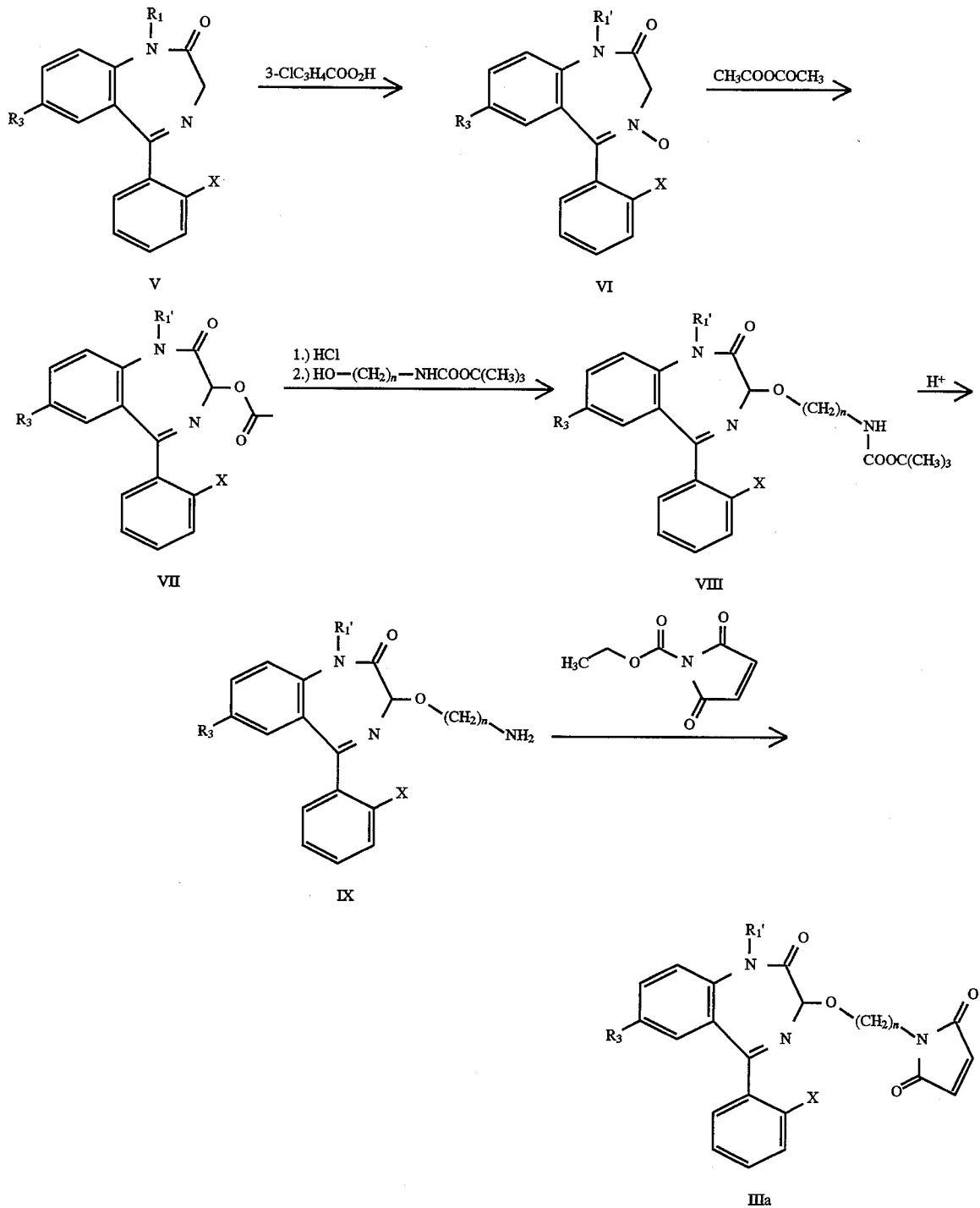

(Diagram 1)

Benzodiazepines of the formula V, for example, are oxidized with the aid of metachloroperbenzoic acid to the formula VI and, under structural rearrangement, acylated used in a reaction to give benzodiazepine-3-oxyethylmaleimides and/or oxypropylmaleimides of the formula III with R2'=OR'.

If, in formula III, R1' is equal to R', a benzodiazepine compound of the formula X with N protected bromoethylamine is alkylated and the amide group is hydrolytically cleaved to give the amine (compound of the formula XI). The 1-ethylmaleimides of the formula III are obtained, for example, in a reaction with ethoxycarbonylmaleimide.

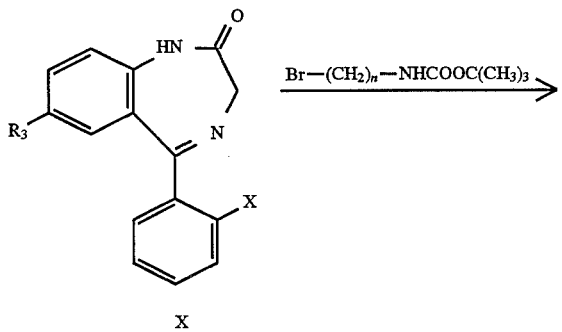

X

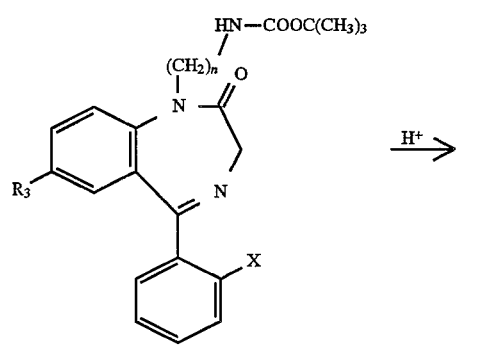

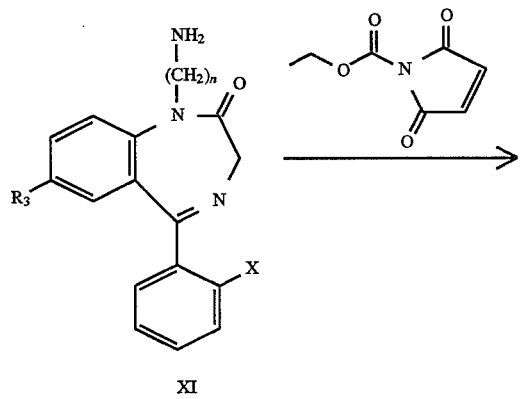

XI

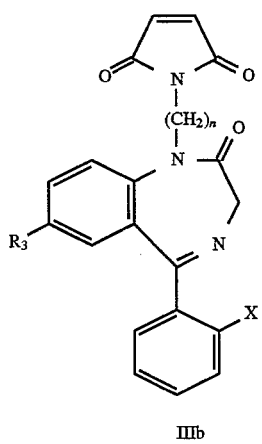

IIIb

EXAMPLE 1

Immunization and Testing of the Antisera

Five sheep are immunized with immunogens according to examples 3 and 4 in Freund's adjuvant. The dose administered to each animal is 500 µg. The immunization procedures are repeated over a period of 6 months or more in intervals of 4 weeks.

Antiserum samples are taken from each animal once a month and tested for the presence of benzodiazepine antibodies. The procedure for this measurement is described in example 2. For additional tests, antisera are selected which provide a sufficiently high measuring signal in dilutions of 1:10000 or higher (at least 100 mA after 30–60 min of color development).

Three months after begin of the immunization, the sera of all animals show a sufficiently high signal.

EXAMPLE 2

Detection of Different Benzodiazepines

Solutions used

Coating buffer: 50 mM sodium bicarbonate; 0.09% sodium azide; pH 9.6

Incubation buffer: 10 mM sodium phosphate; 0.1% Tween 20 (manufactured by Brenntag, Cat. No. 460761; 0.9% NaCl; 1% Crotein C (manufactured by CRODA GmbH, Cat. No. 38241422); pH 7.4

Washing solution: 0.9% NaCl; 0.1% Tween 20

Substrate solution: Enzymun-Test substrate solution (Boehringer Mannheim GmbH, Cat. No. 85742) contains 1.9 mM ABTS and 3.2 mM sodium perborate in phosphate citrate buffer pH 4.4) with 2 mg/ml vanillin.

Procedure

Coating

Microtiter plates (Maxisorp F96, manufactured by Nunc, Cat. No. 4-42404) are coated with streptavidin (Boehringer Mannheim GmbH, Cat. No. 976 539) which is dissolved in a concentration of 5 µg/ml protein in coating buffer. 100 µl of this solution are pipetted into each well of the microtiter plate. After incubation for 1 hour at room temperature, the solution is discarded under shaking, and the plate is washed 3 times with washing solution.

Synthesis of delorazepam biotin conjugate (3)

92.4 mg (0.2 mmol) of trifluoroacetate of (2) are dissolved in 10 ml THF and a solution of 150.6 mg (0.24 mmol) biotin-DDS (prepared according to PCT/EP 94/00195) in 5 ml DMF is added. 50 µl triethylamine are added to the reaction mixture which is then stirred for 16 hours at 20° C. Subsequently, solvent is evaporated under an oil pump vacuum on a rotary evaporator; the residue is taken up in 20 ml of chloroform. The mixture is washed twice with 20 ml of saturated NaHCO₃ and subsequently, the chloroform is removed on the rotary evaporator. The solid product 3 is digested with approximately 5 ml acetic ester, drawn off, and dried overnight in an exsiccator.

Yield: 21 mg (12% of theory) colorless, fine crystalline powder

TLC: silica gel, acetic ester/methanol, 1/1 (v/v); $R_f$=0.48.

The delorazepam-1-DDS-biotin (3) conjugate is dissolved in incubating buffer ad 10 ng/ml. The wells of the microtiter plates are coated each with 100 µl of the solution, subsequently incubated, and washed as described above.

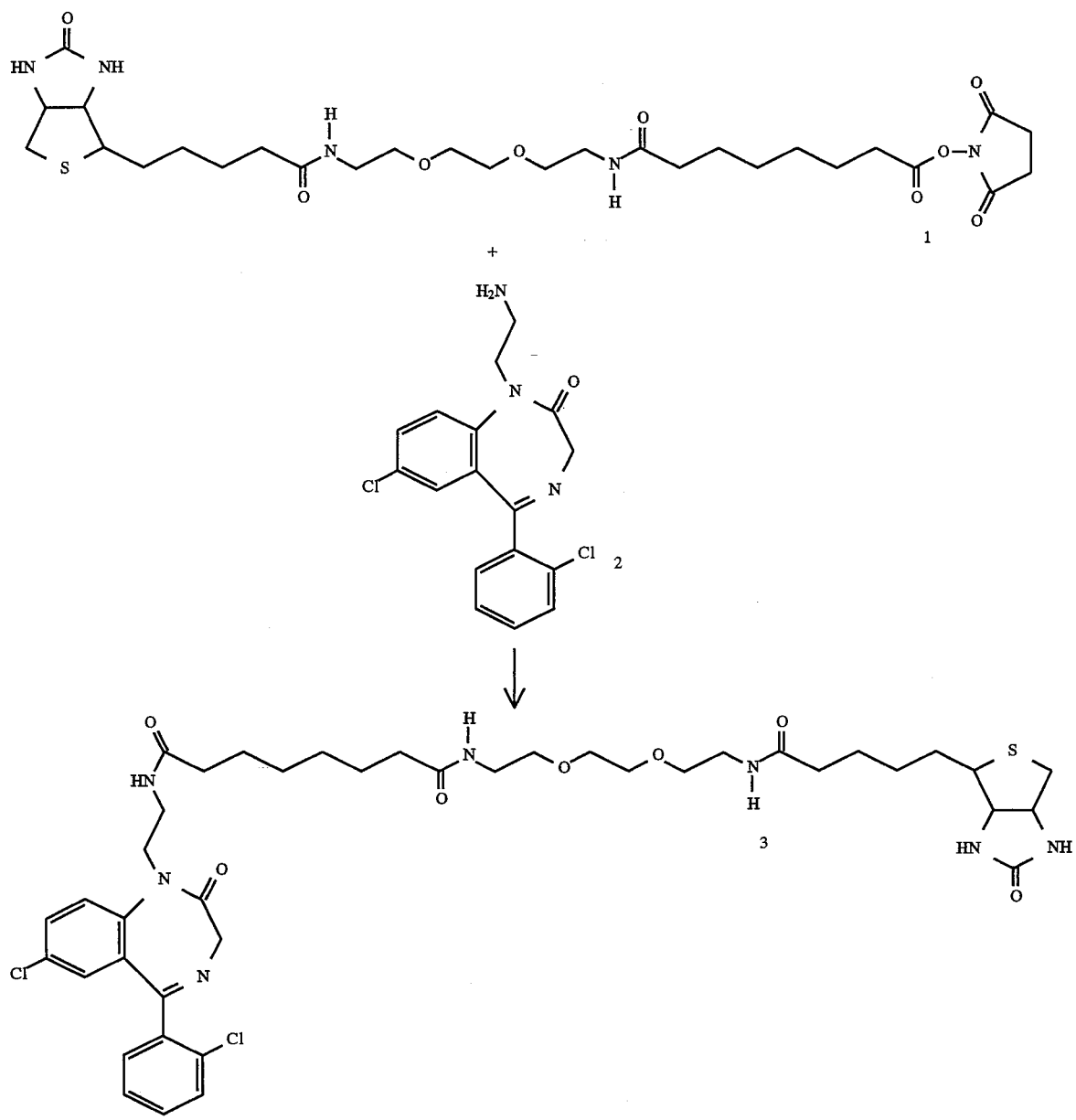

Reaction of the antibodies with the haptens

A dilution series in incubation buffer is prepared from each benzodiazepine compound to be tested. The series includes a total of 10 different concentrations in dilution steps 1:3, starting with the maximum concentration. The maximum concentrations are 1 µg/ml for temazepam, oxazepam, lorazepam, bromazepam, alprazolam, hydroxy-alprazolam, hydroxy-triazolam and amino-flunitrazepam. The maximum concentrations are 10 µg/ml for temazepam-glucuronide, 2-amino-4-chlorobenzophenon, oxazepam glucuronide, lorazepam glucuronide, and 2-amino-2',4-dichlorobenzophenon.

Incubation buffer without hapten is used as a comparison. 50 µl of these solutions are prepared in the wells of the plate.

The antisera are diluted with incubation buffer in a relation of at least 1:10000. Portions of 50 µl of this diluted serum are added into the wells with the hapten solution and mixed. The final concentrations of the haptens and the antibodies in the test is therefore half as high as the one in the solution used.

Incubation (60 minutes) and washing is carried out as described above.

Reaction with the detection conjugate

A conjugate of horseradish-peroxidase and rabbit antibodies to sheep IgG is used to detect the antibodies bound to the solid phase via the hapten biotin conjugate. The detection conjugate is diluted with incubation buffer to 20 min/unit/ml peroxidase activity and the solution is distributed into the wells (100 µl/well).

Incubation (60 min) and washing are carried out as described above.

Substrate reaction

All wells are filled with 100 µl substrate solution and incubated under shaking until the color development in the sample without hapten appears to be sufficient. Then the absorbance of the wells is determined as a difference measurement at a wavelength of 405/492 nm.

Evaluation

A reduction of the measuring signal by at least 20% as compared to the blank value without hapten is considered a positive result (clear detection of the benzodiazepine used). The benzodiazepine concentration which corresponds exactly to this signal value (cut-off value) is determined by means of linear interpolation between the adjacent standards of the hapten series for each of the compounds tested.

Results

Table 1 shows the cut-off values for series of benzodiazepine drugs and their metabolite derivatives: the examples show antisera of 3 or 5 sheep. The serum samples were obtained 12 months after begin of the immunization.

The figures underline that a broad range of benzodiazepines with completely different structures can be detected with a very good to sufficient sensitivity of all three antisera.

TABLE 1

Detection of benzodiazepines
The table gives the benzodiazepine concentrations (ng/ml) which generated a signal reduction by 20% with respect to the blank value without hapten in a competitive ELISA test

| Benzodiazepine | Animal number (serum dilution used) | | |
|---|---|---|---|
| | 1 (1:14000) | 2 (1:16500) | 3 (1:11500) |
| Temazepam | 0.13 | 0.24 | 0.35 |
| 2-amino-4-chlorobenzophenon | 64 | 68 | 69 |
| Temazepam-glucuronide | 2.1 | not calculated | not calculated |
| Oxazepam | 0.29 | 0.26 | 0.41 |
| Oxazepam gluoronide | 7.5 | 8.7 | 11.0 |
| Lorazepam | 1.7 | 1.3 | 2.0 |
| Lorazepam glucuronide | 80 | 7.3 | 49 |
| 2-amino-2',4-dichlorobenzophenon | 270 | 160 | 130 |
| Bromazepam | 5.5 | 150 | 25 |
| Alprazolam | 0.09 | 0.54 | 0.10 |
| Hydroxy-Alprazolam | 0.47 | 5.0 | 0.34 |
| Hydroxy-triazolam | 3.0 | 15 | 9.1 |
| Amino-flunitrazepam | 6.0 | 0.42 | 4.1 |

EXAMPLE 3

Synthesis of 7-chloro-3-[2-(N-maleinimido)ethyl]oxy-1-methyl-5-phenyl-1H-1,4-benzodiazepine-2(3H)on (IIIa)

1. 7-chloro-1-methyl-5-phenyl-1H-1,4-benzodiazepine-2(3H)on-4-oxide (VI)

5.70 g (20 mmol) of 7-chloro-1-methyl-5-phenyl-1H-1,4-benzodiazepine-2(3H)on (manufactured by Sigma, No. T 8275) are dissolved in 150 ml of dichloromethane and 13.8 g (40 mmol) of 3-chloro-peroxybenzoic acid (manufactured by Aldrich, No. 27.303-1) are added under stirring at 20° C. Stirring of the solution is continued for 1.5 h at 20° C. Then the reaction mixture is washed first with 200 ml of 5% $NH_3$ and subsequently with 200 μl of 0.1 n NaOH. The solvent is removed on an rotatione evaporator and the remaining oily residue is dissolved in 25 ml of isopropanol under heating to 40°–45° C. Subsequently, the product is allowed to crystallize under slow cooling down to room temperature. 2 hours after the onset of crystallization, the solid product 2 is drawn off and washed with 50 ml of isopropanol and 50 ml of diisopropylether. The mixture is then dried over night over paraffin in an exsiccator.

Yield: 3.30 g (55% of theory), colorless crystals.
TLC: silica gel, acetic ester/petrol ether 2/1 (v/v); Rf=0.41

2. 3-acetoxy-7-chloro-1-methyl-5-phenyl-1H-1,4-benzodiazepin-2(3H)on (VII)

3.0 g (10 mmol) of compound VI are heated up for 5 hours in 30 ml of THF+60 ml acetic anhydride under reflux. Subsequently, the solution is concentrated on a rotary evaporator and the crystalline residue is digested with 50 ml of isopropylether. The mixture is drawn off and the product is dried for 32 hours in a high vacuum at 50° C.

Yield: 3.27 g (99% of theory) of colorless crystals.
TLC: silica gel, acetic ester/petrolether 2/1 (v/v); Rf=0.50

3. N-(tert. butoxycarbonyl)ethanolamine 30.5 g (0.5 mol) ethanolamine (manufactured by Fluka, No. 02400) are dissolved in 300 ml of dioxane/water 1/1 (v/v) and a solution of 109 g (0.5 mol) of di-tert.-butyldicarbonate (manufactured by Fluka, No. 34659) in 150 ml of dioxane are added dropwise while being cooled on ice. The ice-cooling is removed and the solution is allowed to reach room temperature while being stirred. After another 18 hours, the solution is concentrated on a rotary evaporator, the oily residue is dissolved in 250 ml acetic ester and dried over approximately 20 g of $Na_2SO_4$. After filtration, the solution is again concentrated and the oily residue is dried for 3 hours in a high vacuum.

Yield: 80.2 g (99% of theory) colorless oil.
TLC: silica gel, acetic ester/methanol 1/1 (v/v);
Detection by spraying With ninhydrin solution; Rf=0.74

4. 3-[2-(tert.-butoxycarbonylamino)ethyl]oxy-7-chloro-1-methyl-5-phenyl-1H-1,4-benzodiazepine-2(3H)on (VIII)

1.5 g (5 mmol) of compound VII are dissolved in 50 ml of chloroform (dried over aluminum oxide). While vigorously stirring at 20° C., HCl gas is passed through the solution for a period of 10 min via a capillary tube in a constant flow (approximately 40–50 $cm^3$/min). Subsequently, the mixture is stirred for 18 hours at 20° C. Then the reaction solution is concentrated on the rotary evaporator and dried. The solid residue is dissolved in 20 ml of chloroform (dried over aluminum oxide) and 960 mg (6 mmol) of N.-(tert.-butoxycarbonyl)ethanolamine in 10 ml of the same solvent are added. 500 mg of nafion-NR 50 (manufactured by Aldrich, No. 30.938-9) are added and stirred at 20° C. for 1 h. Then the solution is filtered, washed twice with 50 μl of water each time, dried over aprox. 5 g of $Na_2SO_4$, anhydrous. The solvent is removed on the rotary evaporator. Then, the raw product is dissolved in a lowest possible volume of acetic ester/petrol ether 2/1 (v/v) while slightly heating up and purified via column chromatography on silica gel (column: 4×68 cm, eluent: acetic ester/petrol ether 2/1 (v/v)). The corresponding fractions are collected, the solvent is removed on the rotary evaporator, and the crystalline product is dried for 2 h in a high vacuum at 50° C.

Yield: 1.22 g(55% of theory), colorless crystals.
TLC: silica gel, acetic ester/petrol ether 2/1 (v/v); Rf=0.44

5. 3-(2-Aminoethyl)oxy-7-chloro1-methyl-5-phenyl-1H-1,4-benzo-diazepine-2(3H)one hydrochloride (IX)

1.11 g (2.5 mmol) of compound VIII are dissolved in 10 ml of 2 molar HCl in dioxane. An oily precipitate is formed within a few minutes. The suspension is allowed to stand for 30 min at 20° C., the solvent is decanted, and the remainder is digested with 20 ml of acetic ester with the product being solidified. The suspension is stirred for 1 h at 20° C., drawn off and the hydrochloride is dried for 4 h at 40° C. in a high vacuum.

Yield: 910 mg (96% of theory), colorless, fine crystalline powder.

TLC: silica gel, n-butanol/glacial acetic acid/water 50// 15/25 (v/v/v); Rf=0.64

6. 7-Chloro-3-[2-(N-maleinimido)ethyl]oxy-1-methyl-5-phenyl-1H-1,4-benzodiazepine-2(3H)one (IIIa)

760 mg (2 mmol) of compound IX are suspended at 20° C. in 10 ml of saturated sodium bicarbonate solution; 340 mg (2 mmol) of N-methoxycarbonylmaleinimide (manufactured by Fluka, No. 64940) are added under stirring. After approx. 2–3 min. an oily precipitate forms. After another 10 min, 15 ml of tetrahydrofurane are added and stirred for another 45 min at 20° C. Then, concentrated HCl is used to adjust the reaction mixture to a pH of 6.0, then it is extracted with 50 ml of acetic ester and the extract is washed with 2×50 ml of water. The organic solution is dried with approx. 5 g of $Na_2SO_4$, concentrated on the rotation evaporated, and the remaining raw product is purified via column chromatography on silica gel (column: 2.5×50 cm, eluent: acetic ester). The corresponding fractions are collected, the solvent on the rotary evaporator is removed and the remaining crystalline maleinimide IIIa is dried for 3 h on a high vacuum at 40° C.

Yield: 315 mg (37% of theory), colorless, fine crystalline solid material.

TLC: silica gel, acetic ester; Rf=0.49

1H-NMR (CDCl3): d(ppm=3.37(s,3H:—CH3), 3.91/4.14 (m; 4H;—CH2—CH2—), 4.87(s,1H;—C3H—),6.69(s, 2H;—CH=CH—), 7.48(m; 8H; aromatics H).

EXAMPLE 4

Synthesis of 7-chloro-5-(2-chlorophenyl)-1-[2-(N-maleinimido)ethyl]-1H-1,4-benzodiazepine-2(3H) one (IIIb)

1. N-(tert.-butoxycarbonyl)-2-bromoethylamine 10.2 g (50 mmol) of 2-bromoethylamine hydrobromide (manufactured by Aldrich, No. B6,570-5) are dissolved in 100 ml of dioxane/water 1/1 (v/v) and 15 g (20.6 ml) of triethylamine are added. The mixture is then cooled to 0° C. and a solution of 10.9 g (50 mmol) of di-tert.-butyldicarbonate in 15 ml of dioxane are added dropwise under stirring. The reaction mixture is allowed to slowly reach room temperature and stirring is continued for 18 h. The solvent is removed on the rotary evaporator and the remainder is taken up in 200 ml of acetic ester. It is then washed three times with 100 ml of saturated sodium bicarbonate solution each time and subsequently twice, each time with 100 ml of water. The organic solution is dried with approx. 20 g of $Na_2SO_4$, the solvent is removed on the rotary evaporator and the oily product is dried for 3 h at 40° C. in a high vacuum.

Yield: 12.0 g (98% of theory), slightly brownish, viscous oil.

TLC: silica gel, acetic ester: Rf=0.90

2. 7-Chloro-1-[2-(tert.-butoxycarbonylamino)ethyl]-5-(2-chlorophenyl)-1H-1,4-benzodiazepine-2(3H)one 3.05 g (10 mmol) of 7-chloro-5-(2-chlorophenyl)-1H-1,4-benzodiazepine-2(3)one (manufactured by Sigma, No. D 7662) are dissolved in 20 ml of dimethylformamide and cooled down to 0° C. under the exclusion of air ($N_2$ atmosphere). 480 mg (20 mmol) of sodium hydride (suspension in paraffin oil; manufactured by Merck. No. 818023) are added to the slightly yellow solution which is then stirred for 10 min at 0° C. The reaction mixture then changes color to orange brown. Subsequently, 2.69 g (12 mmol )N-(tert. -butoxycarbonyl)-2-bromoethylamine are added to the solution and allowed to slowly reach room temperature. The solution is stirred for 18 h at 20° C., then the mixture is poured on ice and product is purified via preparative column chromatography on silica gel (column: 4×68 cm, eluent: acetic ester). The corresponding fractions are collected, the solvent is removed on the rotary evaporator and the remaining solid material is dried for 1 h at a high vacuum at 40° C.

Yield: 2.66 g (59% of theory) colorless, fine crystalline powder

TLC: silica gel, acetic ester: Rf=0.6

3. 1-[2-aminoethyl]-7-chloro-5-(2-chlorophenyl)-1H-1,4-benzodiazepine-2(3H)one trifluoroacetate (XI)

2.24 g (5 mmol) of the compound of 2. are dissolved in 50 ml of acetic ester and cool down to 0° C. 10 ml of trifluoroacetic acid are added dropwise under stirring and stirring is continued for another 30 min. Subsequently, the acid and solvent are removed on the rotary evaporator and product XI is dried for 5 h at 40° C. in a high vacuum.

Yield: 2.32 g (100% of theory) of slightly yellowish, fine crystalline powder.

TLC: silica gel, n-butanol/glacial acetic ester/water 50/15/25 (v/v/v); Rf=0.74

4. 7-chloro-5-(2chlorophenyl )-1-[2-(N-maleinimidoethyl]-1H-1,4-benzo-diazepin-2(3H)one (IIIb)

1.16 g (2.6 mmol) of the trifluoroacetate XI are suspended at 20° C. in 15 ml of saturated sodium bicarbonate solution and 425 mg (2.5 mmol) of N-methoxycarbonylmaleinimide in 20 ml tetrahydrofurane are added under stirring. Stirring is continued for 1 h at 20° C. Subsequently, concentrated HCl is used to adjust the reaction mixture to a pH of 6.0; the solution is extracted with 50 ml of acetic acid, and the extract is washed with 2×50 ml of water. The organic solution is dried with approx. 5 g of $Na_2SO_4$, concentrated on the rotary evaporator and the remaining raw product is purified via column chromatography on silica gel (column: 2.5×50 cm, eluent: acetic ester). The corresponding fractions are collected, the solvent is removed on the rotary evaporator, and the remaining crystalline maleinimide lib is dried for 3 h at 40° C. in high vacuum.

Yield: 330 mg (31% of theory) colorless, fine crystalline solid material

TLC: silica gel, acetic ester; Rf=0.60

1H-NMR(CDCl3): d(ppm)=3.86/4.10(m,4H;—CH2—CH2—),3.80/4.86 (AB-Signal,J=12 Hz,2H;—C3H2—), 6.70(s,2H;—CH=CH—), 7.32(m,7H; aromatic H).

We claim:

1. A benzodiazepine protein conjugate of the formula I

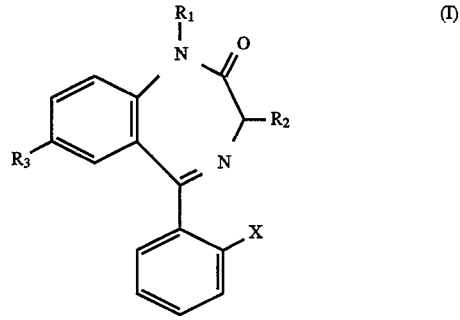

wherein $R_1$ is selected from the group consisting of hydrogen, a methyl group and R;

$R_2$ is selected from the group consisting of hydrogen, a hydroxyl group and an OR group, with the proviso that when $R_1$ is hydrogen or a methyl group, then $R_2$ is an OR group; and with the further proviso that when $R_2$ is hydrogen or a hydroxyl group, then $R_1$ is R;

$R_3$ is selected from the group consisting of halogen, $NO_2$ and $NH_2$;

X is selected from the group consisting of hydrogen or halogen; and

R is a group of the formula II

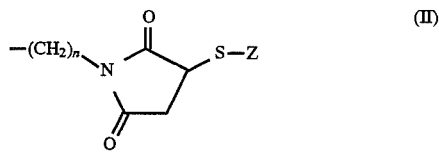
(II)

wherein Z is a macromolecular immunogenically active carrier substance and n is 2 or 3.

2. The benzodiazepine protein conjugate of claim 1, wherein n is 2.

3. The benzodiazepine protein conjugate of claim 1, wherein the macromolecular immunogenically active carrier substance is selected from the group consisting of a polypeptide and an enzyme.

4. The benzodiazepine protein conjugate of claim 3, wherein the immunogenically active carrier substance is a polypeptide and the polypeptide is selected from the group consisting of KLH, edestin and bovine serum albumin.

5. The benzodiazepine protein conjugate of claim 3, wherein the immunogenically active carrier substance is an enzyme and the enzyme is β-galactosidase.

6. The benzodiazepine protein conjugate of claim 1, wherein in at least one of $R_3$ and X is selected from the group consisting of fluorine, chlorine, bromine and iodine.

7. The benzodiazepine protein conjugate of claim 1, wherein at least one of $R_3$ and X is chlorine.

8. The benzodiazepine protein conjugate of claim 1, wherein the benzodiazepine protein conjugate is selected from the group consisting of a compound of the formula Ia and a compound of the formula Ib

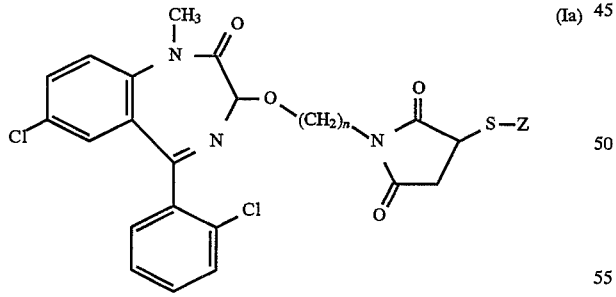
(Ia)

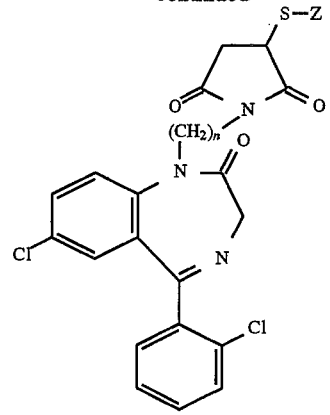
(Ib)

wherein Z is a macromolecular immunogenically active carrier substance and n is 2 or 3.

9. A benzodiazepine linker compound of the formula III, said benzodiazepine linker compound being suitable for preparing a benzodiazepine protein conjugate of claim 1,

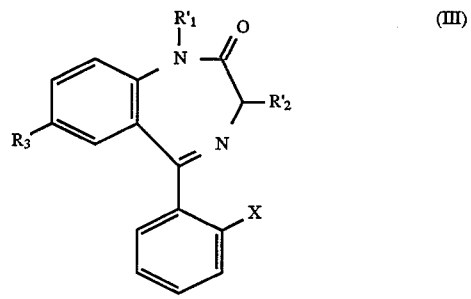
(III)

wherein $R_1'$ is selected from the group consisting of hydrogen, a methyl group and R';

$R_2'$ is selected from the group consisting of hydrogen, a hydroxyl group and an OR' group, with the proviso that when $R_1'$ is hydrogen or a methyl group, then $R_2'$ is an OR' group; and with the further proviso that where $R_2'$ is hydrogen or a hydroxyl group, then $R_1'$ is R';

$R_3$ is selected from the group consisting of halogen, $NO_2$ and $NH_2$;

X is selected from the group consisting of hydrogen or halogen; and

R' is a group of the formula IV

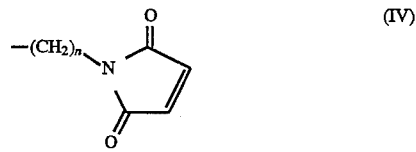
(IV)

wherein n is 2 or 3.

* * * * *